United States Patent [19]

Strawn

[11] Patent Number: Plant 5,436

[45] Date of Patent: Apr. 16, 1985

[54] COTTONTAIL—MINIATURE ROSE PLANT

[75] Inventor: Leslie E. Strawn, Garden Grove, Calif.

[73] Assignee: Cecelia Lucy Daphne Bennett, Chula Vista, Calif.

[21] Appl. No.: 528,652

[22] Filed: Sep. 1, 1983

[51] Int. Cl.[3] ..... A01H 5/00

[52] U.S. Cl. ..... Plt./8

[58] Field of Search ..... Plt./8, 9

*Primary Examiner*—Robert E. Bagwill

[57] ABSTRACT

The subject of the present disclosure is a new and distinct variety of miniature rose plant, named "Cottontail", which is characterized by its vigorous growth habit and abundance of white blooms, borne usually on sprays of 6 to 12 or more blooms.

1 Drawing Figure

The present invention relates to a new and distinct variety of a hardy, dwarf, miniature bush plant of the miniature class; the variety being primarily characterized as a white.

The variety is further characterized by:

A plant of vigorous growth rapid, ranging from 24 to 48 inches in all dimensions. The branches are sturdy and erect, heavily branched with above average foliage covering.

The plant is an extremely prolific bloomer, producing inflorescences of 5 to 7 sprays or more, each containing 6 to 12 or more blooms. The combination of vigorous growth and abundant bloom produce a plant of attractive appearance that does well in either the green house or outdoors.

The seed parant was Pink Petticoat (Miniature Rose Plant, pink blend; Leslie E. Strawn; introduced by Pixie Treasures, 1979) and the pollen parent was unknown.

Subsequent to the origination of the variety, the plant was successfully reproduced at Tiny Petals Nursery located in the county of San Diego, State of California, retaining the distinguishing characteristics through succeeding propagations by cuttings.

The descriptive matter which follows pertains to roses grown and color values observed in plants and newly opened blooms in the months of May through July. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant named "Cottontail", the following is a detailed description thereof in outline; all major color plate identifications being by reference to The British Colour Council Horticultural Colour Chart, except where common terms of color definition are employed.

Type: Hardy, dwarf, bushy, green house or outdoor, garden decoration rose plant.

Class: Miniature.

Variety name: Cottontail

Flowers borne: One to a stem or in sprays of 6 to 12 or more blooms and in inflorescences of 5 to 7 sprays with foliage well below the blooms.

Quantity of bloom: Very prolific both outdoors or green house grown.

Bud.

*Peduncle.*—Varies in length from average to long (25 to 35 mm); average diameter and sturdy; near Pod Green (061 to 061/1 page 120).

*Hairs.*—Extremely small and abundant over the entire surface of the peduncle, calyx tube and sepals.

*Calyx.*—Color is near Pod Green (061 to 061/1 page 120).

*Opening.*—Opens well in all weather.

Bloom:

*Size when fully open.*—Average for a miniature variety (30 to 40 mm).

*Petalage.*—Double — Averaging about 30 to 36 petals, arranged regularly plus petaloids (14 to 20 or more).

*Form.*—Urn-shaped in the bud stage becoming globular before the bloom finally opens. Fully open, the bloom has a "chrysanthemum-like" appearance, heavily petaled in a rounded spreading form with the outermost rows of petals reflexing downward.

Petals: Fairly thick with good substance; matte finish on both the upper and under surfaces.

*Shape.*—Obovate form with a slight peak at the apex.

Color (newly opened flowers from plants grown outdoors, May through July 1983, Chula Vista, Calif.):

*All petals and petaloids.*—White on upper and under surfaces. The petals may exhibit a slight pink cast prior to petal maturation.

*General effect.*—Bright white 'pom pom' blooms.

*Flower longevity.*—(May through July 1983) Plant in ground 2 to 3 days from bud with sepals down to fully opened bloom. Holding at fully opened for additional 3 to 5 days or more before dropping petals. Cut blooms at livingroom temperature 3 to 5 days or longer.

Reproductive organs:

*Stamens.*—A few arranged uniformily around the pistil.

*Filament.*—Average in length.

*Pollen.*—Slight amount.

*Pistil.*—Very small; pale green in color.

*Styles.*—Very short; pale green in color.

*Ovaries.*—All encased in calyx.

*Hips.*—Some.

*Seeds.*—Few or none.

*Sepals.*—Permanent; lanceolate-shaped; recurves against the peduncle as the bloom opens.

Foliage: p2 *Leaves.*—Five to seven leaflets on the average; medium size for a miniature rose plant.

*Leaflets.*—Broad ovate-shaped.

*Margin.*—Very serrated with occasional bronzing on the newer foliage.

*Color.*—Ranging from near Spinach Green (0960 to 0960/1 page 187) to near Scheeles Green (860 to 860/1 page 175) with some bronze on the margins of the newer foliage. The upper surfaces have a satiny finish, and the under surfaces have a matte finish of a slightly light shade than the upper surfaces.

*Rachis.*—Medium strength; upper surface is grooved; under surface has a few pale yellow thorns which are hooked; both upper and under surfaces have numerous small hairs.

*Stipules.*—Small to average in length; average width; tapering auricles angled outward at about 45 degrees.

Growth:

*Habit.*—Dwarf, bushy, much branched; very large for a miniature rose plant.

*Growth.*—Extremely vigorous.

*Canes.*—Large; sturdy; held very erect, except when the weight of very large inflorescences may bend them down (i.e. an inflorescence of 50 to 75 blooms).

*Main stems.*—Color — Ranging from near Pod Green (061 to 061/1 page 120) to near Scheeles Green (860 to 860/1 page 175).

*Thorns.*—Pale Yellow to Reddish on the main stems; long, slender and hooked downward.

*Branches.*—Color — Ranging from near Pod Green (061 to 061/1 page 120) to near Scheeles Green (860 to 860/1 page 175). Medium to long in length; study; very erect. Thorns — As described above. Prickles — Some. Hairs — None.

The miniature rose plant and its flowers as herein described may vary in slight detail due to climatic, soil, and cultural conditions under which the variety may be grown; the present description being of the variety as grown at Chula Vista, Calif.

The following is claimed:

1. A new and distinct variety of miniature rose plant named "Cottontail" of hardy, dwarf, bushy, much branched habit, substantially as illustrated and described, characterized by its abundance of white blooms and having an extremely vigorous growth habit, easy to propagate from cuttings, with flowers usually borne in sprays of 6 to 12 or more.

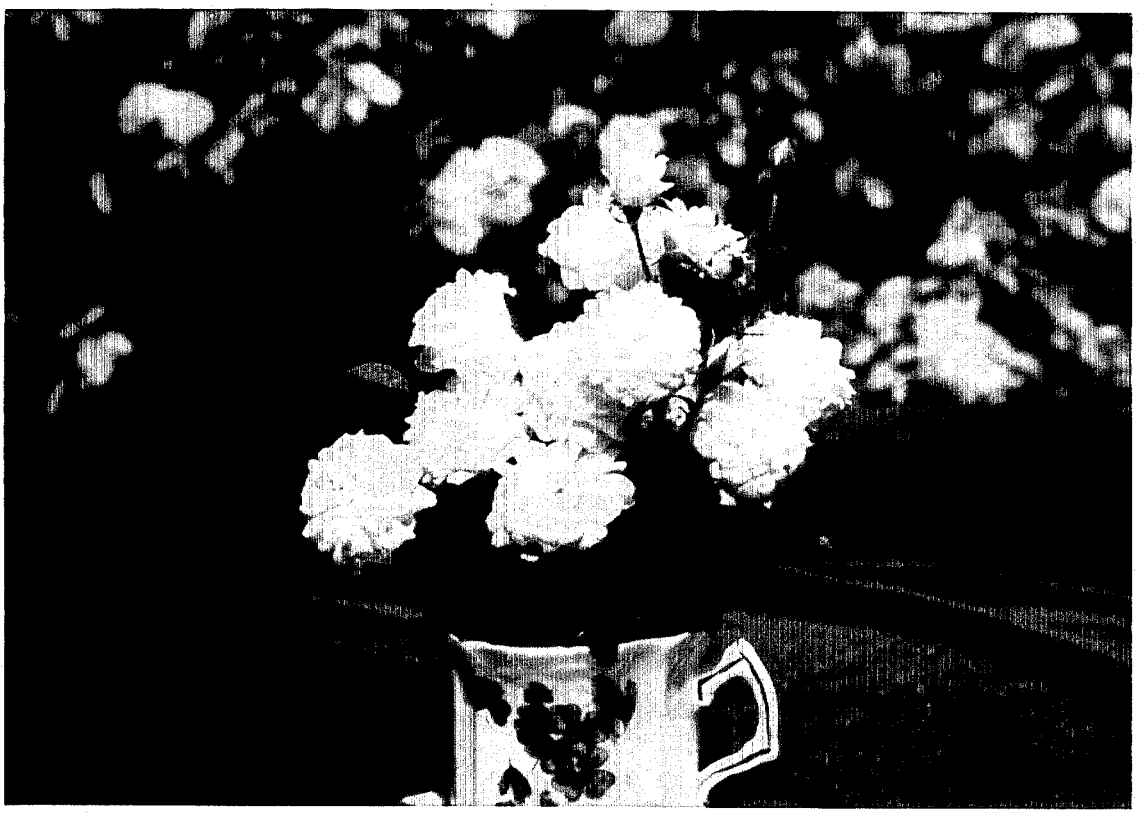

* * * * *